US011155481B2

(12) United States Patent
Dhawan et al.

(10) Patent No.: US 11,155,481 B2
(45) Date of Patent: Oct. 26, 2021

(54) USE OF CATIONIC SUGAR-BASED COMPOUNDS FOR MICROBIAL FOULING CONTROL IN A WATER SYSTEM

(71) Applicant: ECOLAB USA INC., Saint Paul, MN (US)

(72) Inventors: Ashish Dhawan, Saint Paul, MN (US); Kun Xiong, Saint Paul, MN (US); Carter M. Silvernail, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

(21) Appl. No.: 16/775,417

(22) Filed: Jan. 29, 2020

(65) Prior Publication Data

US 2020/0239339 A1   Jul. 30, 2020

Related U.S. Application Data

(60) Provisional application No. 62/798,193, filed on Jan. 29, 2019.

(51) Int. Cl.
*C02F 1/68* (2006.01)
*C07H 15/04* (2006.01)

(52) U.S. Cl.
CPC ............ *C02F 1/68* (2013.01); *C07H 15/04* (2013.01); *C02F 2303/20* (2013.01)

(58) Field of Classification Search
USPC ..................................... 210/749; 422/7, 28
See application file for complete search history.

(56) References Cited

U.S. PATENT DOCUMENTS

| | | | |
|---|---|---|---|
| 3,794,586 A | 2/1974 | Kimura et al. | |
| 4,259,217 A | 3/1981 | Murphy | |
| 4,355,071 A | 10/1982 | Chang | |
| 4,705,665 A * | 11/1987 | Malik | C09K 8/74 134/3 |
| 4,784,797 A | 11/1988 | Treybig et al. | |
| 5,053,150 A | 10/1991 | Emert et al. | |
| 5,399,746 A | 3/1995 | Steiger et al. | |
| 5,614,616 A | 3/1997 | Buysch et al. | |
| 5,670,464 A | 9/1997 | Kita et al. | |
| 5,738,795 A | 4/1998 | Chen | |
| 6,004,466 A * | 12/1999 | Derian | C02F 1/444 134/10 |
| 6,054,054 A | 4/2000 | Robertson et al. | |
| 6,080,323 A * | 6/2000 | Yu | A01N 43/16 210/758 |
| 6,090,754 A * | 7/2000 | Chan | B01F 17/0085 507/110 |
| 6,503,880 B1 | 1/2003 | Skold et al. | |
| 6,797,785 B1 | 9/2004 | Hund et al. | |
| 6,881,710 B1 | 4/2005 | O'Lenick, Jr. et al. | |
| 7,052,614 B2 * | 5/2006 | Barak | C02F 1/722 210/752 |
| 7,084,129 B1 * | 8/2006 | Smith | A61K 31/70 514/53 |
| 7,345,015 B1 * | 3/2008 | Kong | C11D 1/662 510/238 |
| 7,507,399 B1 | 3/2009 | O'Lenick, Jr. | |
| 7,604,978 B2 * | 10/2009 | Eldridge | C07K 14/28 435/244 |
| 8,324,264 B1 * | 12/2012 | Eldridge | C07D 413/08 514/406 |
| 8,933,055 B2 * | 1/2015 | Pedersen | A61P 31/12 514/54 |
| 9,956,153 B2 * | 5/2018 | Emiru | A61K 9/122 |
| 10,850,999 B2 * | 12/2020 | DiMascio | B01J 19/305 |
| 10,945,431 B2 * | 3/2021 | Karandikar | C11D 3/30 |
| 2001/0044393 A1 | 11/2001 | Peterson, Jr. et al. | |
| 2002/0155978 A1 | 10/2002 | Man et al. | |
| 2003/0121532 A1 * | 7/2003 | Coughlin | B08B 9/057 134/7 |
| 2005/0215461 A1 | 9/2005 | Gluck et al. | |
| 2006/0008496 A1 | 1/2006 | Kulkarni et al. | |
| 2006/0289164 A1 | 12/2006 | Smith et al. | |
| 2008/0152567 A1 * | 6/2008 | Killough | A22B 7/00 423/243.01 |
| 2010/0029530 A1 | 2/2010 | Whiteley | |
| 2010/0305014 A1 | 12/2010 | Miralles et al. | |

(Continued)

FOREIGN PATENT DOCUMENTS

| | | |
|---|---|---|
| CN | 101972612 A | 2/2011 |
| CN | 104130335 A | 11/2014 |

(Continued)

OTHER PUBLICATIONS

International Search Authority, in connection with PCT/2020/015567 filed Jan. 29, 2020, "The International Search Report and the Written Opinion of the International Searching Authority, or the Declaration", 13 pages, dated Apr. 28, 2020.

Fan et al., "Synthesis and Aggregation Behavior of a Hexameric Quaternary Ammonium Surfactant", Langmuir, vol. 27, pp. 10570-10579, Jul. 28, 2011.

Kawakami et al., "Antibacterial Activity of Radial Compounds with Peripheral Quaternary Ammonium Units", Transactions of the Materials Research Society of Japan, vol. 35[4], pp. 885-887, 2010.

Zhang et al., "PAMAM-Based Dendrimers with Different Alkyl Chains Self-Assemble on Silica Surfaces: Controllable Layer Structure and Molecular Aggregation", J. Phys. Chem. B, vol. 122, pp. 6648-6655, Jun. 13, 2018.

(Continued)

*Primary Examiner* — Nina Bhat
(74) *Attorney, Agent, or Firm* — McKee, Voorhees & Sease, PLC

(57) ABSTRACT

Described herein are the methods of using a cationic alkyl polyglycoside in a fouling control composition to reduce microbial and/biofilm growth in a water system. The described methods or compositions are found to be effective than those methods or compositions including commonly used single quaternary compounds for reducing microbial or biofilm growth in water systems.

23 Claims, No Drawings

(56) References Cited

U.S. PATENT DOCUMENTS

| | | | |
|---|---|---|---|
| 2011/0112007 A1 | 5/2011 | Hodge et al. | |
| 2012/0053111 A1 | 3/2012 | Hodge et al. | |
| 2012/0070341 A1 | 3/2012 | Eder et al. | |
| 2012/0258157 A1* | 10/2012 | Koltzenburg | D06M 15/09 424/409 |
| 2013/0266669 A1 | 10/2013 | Jiang et al. | |
| 2014/0124454 A1 | 5/2014 | Nichols et al. | |
| 2014/0224733 A1 | 8/2014 | Osness et al. | |
| 2015/0203738 A1 | 7/2015 | Witham et al. | |
| 2015/0290100 A1 | 10/2015 | Eder et al. | |
| 2016/0010035 A1 | 1/2016 | Liu et al. | |
| 2016/0030315 A1 | 2/2016 | Emiru et al. | |
| 2016/0262999 A1 | 9/2016 | Pedersen et al. | |
| 2016/0264744 A1 | 9/2016 | Boday et al. | |
| 2017/0029691 A1 | 2/2017 | Faust, Jr. et al. | |
| 2017/0121560 A1 | 5/2017 | Dockery et al. | |
| 2017/0233643 A1 | 8/2017 | Agashe et al. | |
| 2017/0360040 A1 | 12/2017 | Kost et al. | |
| 2018/0007895 A1* | 1/2018 | Karandikar | C11D 3/33 |
| 2018/0066211 A1 | 3/2018 | Pickering et al. | |
| 2018/0118999 A1 | 5/2018 | Hikem et al. | |
| 2018/0163020 A1 | 6/2018 | Zong et al. | |
| 2019/0062187 A1 | 2/2019 | Dhawan et al. | |
| 2019/0223434 A1* | 7/2019 | Balasubramanian | A01N 43/16 |
| 2019/0224627 A1* | 7/2019 | Glanz | B01D 61/10 |

FOREIGN PATENT DOCUMENTS

| | | |
|---|---|---|
| CN | 104130351 A | 11/2014 |
| CN | 105076201 A | 11/2015 |
| CN | 105523956 A | 4/2016 |
| CN | 106172434 A | 12/2016 |
| CN | 106946743 A | 7/2017 |
| CN | 107440935 A | 12/2017 |
| CN | 108033895 A | 5/2018 |
| CN | 108048249 A | 5/2018 |
| CN | 108938662 A | 12/2018 |
| EP | 0296441 A2 | 12/1988 |
| GB | 847321 | 9/1960 |
| JP | 2012136504 A | 7/2012 |
| JP | 2014009177 A | 1/2014 |
| WO | 2004056843 A2 | 7/2004 |
| WO | 2012083497 A1 | 6/2012 |
| WO | 2013087287 A1 | 6/2013 |
| WO | 2014079621 A1 | 5/2014 |
| WO | 2015084304 A1 | 6/2015 |
| WO | 2016205513 A1 | 12/2016 |
| WO | 2017201076 A1 | 11/2017 |
| WO | 2018112548 A1 | 6/2018 |
| WO | 2019046409 A1 | 3/2019 |

OTHER PUBLICATIONS

Zhou et al., "Cooperative binding and self-assembling behavior of cationic low molecular-weight dendrons with RNA molecules", Organic & Biomolecular Chemistry, vol. 4, pp. 581-585, 2006.

Brycki et al., "The biodegradation of monomeric and dimeric alkylammonium surfactants", Journal of Hazardous Materials, vol. 280, pp. 797-815, Aug. 6, 2014.

Gan et al., "Sugar-Based Ester Quaternary Ammonium Compounds and Their Surfactant Properties", Journal of Surfactants and Detergents, vol. 17, Issue 3, pp. 465-470, Jan. 3, 2014.

Negm et al., "Synthesis, Characterization and Biological Activity of Sugar-Based Gemini Cationic Amphiphiles", Journal of Surfactants and Detergents, vol. 11, Issue 3, pp. 215-221, Apr. 26, 2008.

Tan et al., "The use of quaternised chitosan-loaded PMMA to inhibit biofilm formation and downregulate the virulence-associated gene expression of antibiotic-resistant *Staphylococcus*", Biomaterials, vol. 33, Issue 2, pp. 365-377, Jan. 2012.

Zaky, Mohamad, "Biocidal Activities of Cationic Surface Active Starch and Its Transition Metal Complexes Against Different Bacterial Strains", Journal of Surfactants and Detergents, vol. 13, Issue 3, pp. 255-260, Jul. 2010.

Zhi et al., "Self-aggregation and antimicrobial activity of saccharide-cationic surfactants", Colloids and Surfaces A: Physicochemical and Engineering Aspects, vol. 456, pp. 231-237, Aug. 2014.

Labade et al., "Cesium fluoride catalyzed Aza_Michael addition reaction in aqueous media", Monatsh Chem., vol. 142, pp. 1055-1059, Jun. 8, 2011.

Somerscales, Euan F.C., "Fundamentals of Corrosion Fouling", Experimental Thermal and Fluid Science, vol. 14, pp. 335-355, 1997.

Miller et al., "Non-viral CRISPR/Cas gene editing in vitro and in vivo enabled by synthetic nanoparticle co-delivery of Cas9 mRNA and sgRNA", Angew Chem Int Ed Engl., vol. 56(4), pp. 1059-1063, Jan. 19, 2017.

"Azamethonium", http://pubchem.ncbi.nlm.nih.gov/compound/9383, last modified Oct. 6, 2018 and accessed by Applicant Oct. 11, 2018.

Zhang et al., "Controllable Self-Assembly of Amphiphilic Dendrimers on a Silica Surface: The Effect of Molecular Topological Structure and Salinity", Journal of Physical Chemistry, vol. 8, pp. 10990-10999, Oct. 5, 2016.

Zhang et al., "Supporting information", Beijing National Laboratory for Molecular Sciences, published with Controllable Self-Assembly of Amphiphilic Dendrimers on a Silica Surface, 4 pages, Oct. 5, 2016.

Zielinski et al., "Synthesis of new quaternary ammomium salts for organophilization of fillers for polymeric nanocomposites", www.miesiecznikchemik.pl, 2007.

* cited by examiner

USE OF CATIONIC SUGAR-BASED COMPOUNDS FOR MICROBIAL FOULING CONTROL IN A WATER SYSTEM

CROSS-REFERENCE TO RELATED APPLICATION

This application claims priority under 35 U.S.C. § 119 to Provisional Application U.S. Ser. No. 62/798,193, filed on Jan. 29, 2019, which is herein incorporated by reference in its entirety including without limitation, the specification, claims, and abstract, as well as any figures, tables, or examples thereof.

FIELD OF THE INVENTION

The present disclosure relates generally to the field of microbial fouling or biofilm control in a water system, using one or more cationic alkyl polyglycosides. In particular, the present disclosure relates to using a fouling control composition comprising one or more cationic alkyl polyglycosides for microbial fouling control in a water system. The disclosed methods and fouling control compositions disclosed herein are effective to prevent bacteria and biofilm growth in a water system and more environmentally friendly, since the cationic alkyl polyglycosides can be derived from compounds in natural resources and degraded to natural products.

BACKGROUND OF THE INVENTION

A water system, including an industrial water system, serves many different purposes. Any water system, including its equipment and water, is prone to microbial contamination and fouling. Fouling or deposition of any organic or inorganic material can occur even in an industrial water system that is treated with the best water treatment programs currently available. If a water system is not periodically cleaned, then they will become heavily fouled.

Fouling occur due to microbiological contamination and subsequently microbial and/or biofilm growth. Sources of microbial contamination in industrial water systems are numerous and may include, but are not limited to, air-borne contamination, water make-up, process leaks, and improperly cleaned equipment. Microorganisms causing fouling can establish their microbial communities on any wetable or semi-wetable surfaces of a water system. Evaporative cooling water systems are particularly prone to fouling.

Fouling has a negative impact on a water system, particularly an industrial water system. For example, severe mineral scale (inorganic material) would buildup on any water contact surfaces and any scale provides an ideal environment for microorganism and/or biofilm growth. If fouling or biofilm growth is allowed to progress in a water system, the water system can suffer from decreased operational efficiency, premature equipment failure, and increased health-related risks associated with microbial fouling and/or biofilm growth.

Exopolymeric substances secreted by microorganism aid formation of biofilms as the microbial communities develop on surfaces. These biofilms are complex ecosystems that establish a means for concentrating nutrients and offer protection for microbial growth, so the biofilms can accelerate scale formation, corrosion, and other fouling processes. Not only do biofilms contribute to efficiency reduction of the water system, but they also provide an excellent environment for microbial proliferation and for generating dangerous *Legionella* bacteria. It is therefore important that biofilms and other fouling processes be reduced to the greatest extent possible to minimize the health-related risk associated with *Legionella* and other water-borne pathogens.

Various methods are developed to clean or to remove biofilms and microorganisms associated with the biofilms. While cleaning and removing biofilms are necessary, a better approach is to prevent or reduce fouling or biofilm formation or growth, so the need to clear or remove biofilms is reduced. Cleaning or removing biofilms usually requires operation interruption and introduction of other chemicals. One way to prevent or reduce fouling and/or biofilm formation or growth is to treat a water system with a fouling control agent or fouling control composition. For example, corrosion inhibitors and/or fouling control agents are often added into upstream oil and gas production fluids to protect carbon steel pipelines and infrastructure from corrosion and biofilm growth.

Quaternary ammonium compounds have been used for many years as corrosion inhibitors and fouling control agents. Quaternary ammonium compounds belong to an important subcategory of surfactants because they contain unique properties. A main distinction between quaternary ammonium compounds from other surfactants is their unique structure. Quaternary ammonium compounds consist mainly of two moieties, a hydrophobic group, e.g., long alkyl group, and a quaternary ammonium salt group. The unique positive charge of the ammonium plays a key role, e.g., electrostatic interactions, between the surfactant and surface or different components of biofilms. However, the quaternary ammonium compounds used for such purpose are often bis quaternary species or species quaternized with benzyl chloride that are known to be very hazardous. In additional, governmental regulations exist to release any water containing single quaternary compounds into environment.

Therefore, there is a continuing need for different or alternative quaternary ammonium compounds that are better and safer fouling control agents.

Accordingly, it is an objective of the present disclosure to develop novel fouling control agents having improved fouling control properties.

It is a further objective of the disclosure to develop methods and fouling control compositions to make the fouling control in a water system more environment friendly.

These and other objects, advantages and features of the present disclosure will become apparent from the following specification taken in conjunction with the claims set forth herein.

BRIEF SUMMARY OF THE INVENTION

The exemplary cationic alkyl polyglycoside compounds disclosed herein show their effectiveness for preventing bacteria or biofilm growth in water systems. In a related application, U.S. patent application Ser. No. 16/774,226, filed simultaneously herewith and titled "USE OF CATIONIC SUGAR-BASED COMPOUNDS AS CORROSION INHIBITORS IN A WATER SYSTEM", these cationic alkyl polyglycoside compounds were also demonstrated to be effective for inhibiting corrosion in water systems. Not only are these cationic alkyl polyglycosides preferred because they are derived from natural resources, e.g., polyglycosides and fatty alcohols, and degraded to natural products and are environmentally friendly, but also more effective because they function both as corrosion control agents and microbial/biofilm growth control agents.

In one aspect, provided herein is a fouling control composition, wherein the composition comprises the fouling control composition comprises a cationic alkyl polyglycoside and one or more additional fouling control composition agents, wherein the fouling control composition reduces bacterial growth or biofilm growth in the water system.

In another aspect, disclosed herein is a method of controlling microbial fouling in a water system, wherein the method comprises providing a fouling control composition into a water system to generate a treated water system, wherein the fouling control composition comprises a cationic alkyl polyglycoside and wherein the fouling control composition reduces bacterial growth or biofilm growth in the treated water system. In some embodiments, the fouling control composition further comprises one or more additional fouling control composition agents.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology. Accordingly, the figures and detailed description are also to be regarded as illustrative in nature and not in any way limiting.

DETAILED DESCRIPTION OF THE PREFERRED EMBODIMENT

In the following detailed description, reference may made to the accompanying drawings, schemes, and structures which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Disclosed herein are methods and composition for fouling control in a water system. More particularly, one or more alkyl polyglucosides are used in fouling control compositions or methods disclosed herein. These specific alkyl polyglucosides are derived from polyglucoses.

The embodiments of this disclosure are not limited to any specific compositions and methods which can vary and are understood by skilled artisans. It is further to be understood that all terminology used herein is for describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by —CH$_2$CH$_2$CH$_2$—. For alkylene, cycloalkylene, alkynylene, and alkenylene groups, no orientation of the linking group is implied.

The term "ester" as used herein refers to —R$^{30}$COOR$^{31}$ group. R$^{30}$ is absent, a substituted or unsubstituted alkylene, cycloalkylene, alkenylene, alkynylene, arylene, aralkylene, heterocyclylalkylene, or heterocyclylene group as defined herein. R$^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —R$^{32}$NR$^{33}$R$^{34}$ groups. R$^{32}$ is absent, a substituted or unsubstituted alkylene, cycloalkylene, alkenylene, alkynylene, arylene, aralkylene, heterocyclylalkylene, or heterocyclylene group as defined herein. R$^{33}$ and R$^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of R$^{32'}$NR$^{33'}$R$^{34'}$ groups, wherein R$^{32'}$, R$^{33'}$, and R$^{34'}$ are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —R$^{35}$OH groups. R$^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —R$^{36}$COOH groups. R$^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —R$^{37}$OR$^{38}$ groups. R$^{37}$ is absent, a substituted or unsubstituted alkylene, cycloalkylene, alkenylene, alkynylene, arylene, aralkylene, heterocyclylalkylene, or heterocyclylene group as defined herein. R$^{38}$ is a substituted or unsubstituted alkyl, cycloalkyl, alkenyl, alkynyl, aryl, aralkyl, heterocyclylalkyl, or heterocyclyl group as defined herein.

The term "solvent" as used herein refers to any inorganic or organic solvent. Solvents are useful in the disclosed method or composition as reaction solvents or carrier solvents. Suitable solvents include, but are not limited to, oxygenated solvents such as lower alkanols, lower alkyl ethers, glycols, aryl glycol ethers and lower alkyl glycol ethers. Examples of other solvents include, but are not limited to, methanol, ethanol, propanol, isopropanol and butanol, isobutanol, ethylene glycol, diethylene glycol, triethylene glycol, propylene glycol, dipropylene glycol, glycol ethers, mixed ethylene-propylene glycol ethers, ethylene glycol phenyl ether, and propylene glycol phenyl ether. Water is a solvent too. The solvent used herein can be of a single solvent or a mixture of many different solvents.

Glycol ethers include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether, and the like, or mixtures thereof.

Acids

Generally, acids, as used in this disclosure, include both organic and inorganic acids. Organic acids include, but are not limited to, hydroxyacetic (glycolic) acid, formic acid, acetic acid, propionic acid, butyric acid, valeric acid, caproic acid, gluconic acid, itaconic acid, trichloroacetic acid, urea hydrochloride, and benzoic acid. Organic acids also include dicarboxylic acids such as oxalic acid, malonic acid, succinic acid, glutaric acid, maleic acid, fumaric acid, adipic acid, and terephthalic acid. Combinations of these organic acids can also be used. Inorganic acids include, but are not limited to, mineral acids, such as phosphoric acid, sulfuric acid, sulfamic acid, methylsulfamic acid, hydrochloric acid, hydrobromic acid, hydrofluoric acid, and nitric acid. Inorganic acids can be used alone, in combination with other inorganic acid(s), or in combination with one or more organic acid. Acid generators can be used to form a suitable acid, including for example generators such as potassium fluoride, sodium fluoride, lithium fluoride, ammonium fluoride, ammonium bifluoride, sodium silicofluoride, etc.

Examples of particularly suitable acids in this the methods or compositions disclosed herein include inorganic and organic acids. Exemplary inorganic acids include phosphoric, phosphonic, sulfuric, sulfamic, methylsulfamic, hydrochloric, hydrobromic, hydrofluoric, and nitric. Exemplary organic acids include hydroxyacetic (glycolic), citric, lactic, formic, acetic, propionic, butyric, valeric, caproic, gluconic, itaconic, trichloroacetic, urea hydrochloride, and benzoic. Organic dicarboxylic acids can also be used such as oxalic, maleic, fumaric, adipic, and terephthalic acid.

Percarboxylic Acids and Peroxycarboxylic Acid Compositions

A peroxycarboxylic acid (i.e. peracid) or peroxycarboxylic acid composition can be included in the articles, products, or compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOH)$_n$, in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

A peroxycarboxylic acid composition, as used herein, refers to any composition that comprises one or more peracids, their corresponding acids, and hydrogen peroxide or other oxidizing agents. A peroxycarboxylic acid composition can also include a stabilizer, fluorescent active tracer or compound, or other ingredients, as one skilled in the other would know.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid. Peracids such as peroxyacetic acid and peroxyoctanoic acid may also be used. Any combination of these acids may also be used.

In some embodiments, however, the articles, products, or compositions disclosed herein are free of a peroxycarboxylic acid or peroxycarboxylic acid composition.

Cationic Alkyl Polyglycosides

The fouling control composition disclosed herein comprises a cationic alkyl polyglycoside. Alkyl polyglycosides are characterized by one or more monosaccharide units and at least one hydrophobic alkyl group to one of the hydroxyl groups of the saccharide units. These molecules differ in the saccharide unit, the degree of polymerization (DP) of the saccharide units, the number of alkyl groups, the alkyl chain length, both linear and mono-branched, etc.

When polyglycosides are derived from a glucose-based polymer, they are known as alkyl polyglucosides (APG). Starch is a polymeric carbohydrate consisting of a large number of glucose units joined by glycosidic bonds and has a generic structure of

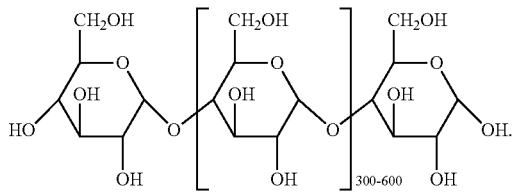

An alkyl polyglucoside, as used herein in this disclosure, is a molecule having one to ten glucose units backbone and at least one alkyl group attached one of the OH groups and has a generic structure of

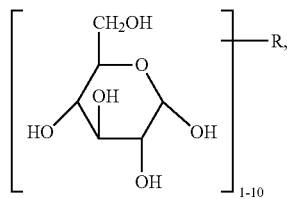

wherein R is an alkyl group and can be attached to any or all of the OH group in the molecule. A cationic alkyl polyglucoside, as used herein in this disclosure, is an alkyl polyglucoside having at least one cationic group in its alkyl group(s).

Within an alkyl polyglucoside or cationic alkyl polyglucoside, the glucose units can be joined together by glycosidic bonds as in starch, by another kind of linkage, through a linker, or a combination thereof. For example, a cationic alkyl glucoside having 2 glucose units has a structure of

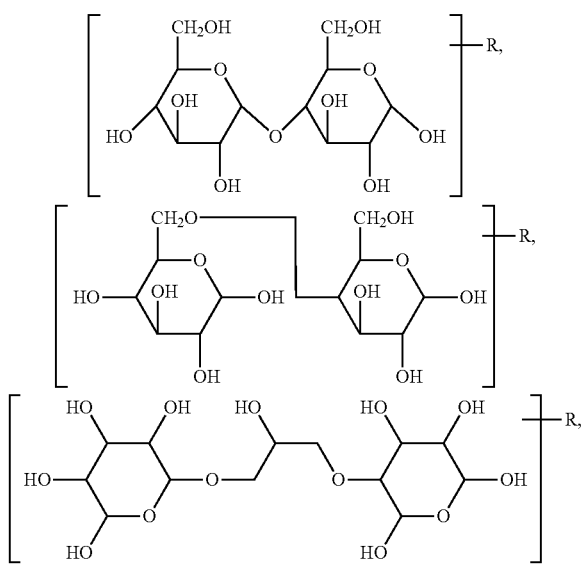

or other linkage with or without a linker between two OH groups in different glucose units. For a cationic alkyl glycoside with three or more glucose units, the linkage between two adjacent glucose units can be the same or different.

A class of alkyl polyglycosides has been widely used as nonionic surfactants in a variety of cosmetic, household, and industrial applications. Alkyl polyglycoside surfactants are usually characterized by one or more saccharide units, which are hydrophilic, in one end and a hydrophobic alkyl group in another end. They are usually derived from polysaccharides from natural resources and fatty alcohols in the presence of acid catalysts at elevated temperatures. The raw materials are typically starch and fat. The final products can be a complex mixture of compounds with different sugar moieties comprising one or more hydrophilic alkyl groups from the fatty alcohol.

As used in this disclosure, an alkyl polyglycoside or alkyl polyglucoside can comprise one or more alkyl groups and the alkyl groups can be different.

In some embodiments, the cationic alkyl polyglucoside can have a generic structure of

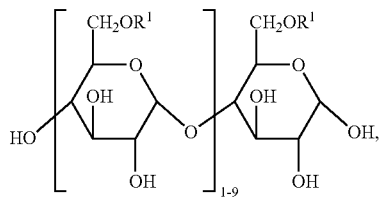

wherein $R^1$ is H or a $C_1$-$C_{30}$ alkyl group and at least one of $R^1$s in the molecule is a $C_1$-$C_{30}$ alkyl group containing a cationic group. In some other embodiments, the cationic alkyl polyglucoside can have a generic structure of

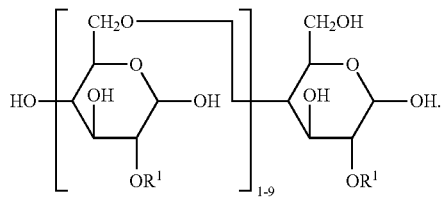

In yet some other embodiments, the cationic alkyl polyglucoside can have a generic structure of

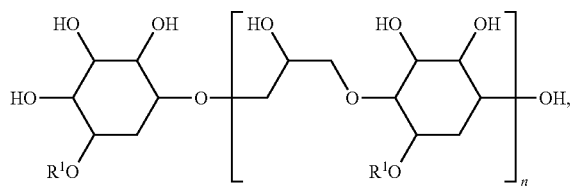

wherein n is from about 1-9 and $R^1$ is H or an $C_1$-$C_{30}$ alkyl group and at least one of $R^1$ is an alkyl group.

A cationic alkyl polyglucoside, as referred in this disclosure, is an alkyl polyglucoside that are described above and have one or more cationic groups. In addition, in some embodiments, a cationic alkyl polyglucoside has a generic structure of

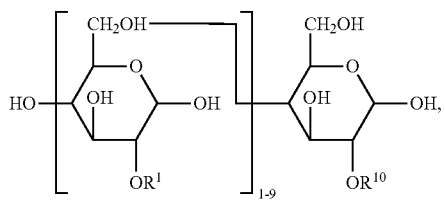

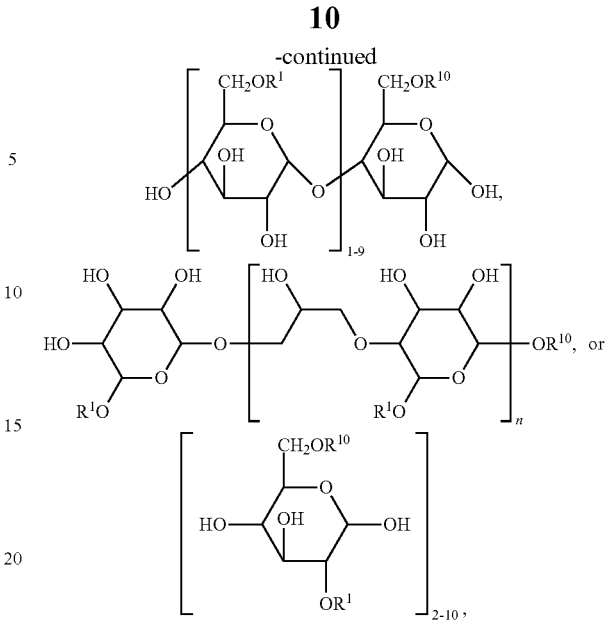

wherein n is 1-9; $R^1$ is H or an $C_1$-$C_{30}$ alkyl group; $R^{10}$ is a $R^{10'}$—$N^+(CH_3)_2R^2$; $R^{10'}$ is a $C_2$-$C_{10}$ alkyl; and $R^2$ is a —$(CH_2)_mCH_3$; and m is 0-21. In some other embodiments, the cationic alkyl polyglucoside has one of the above structures, wherein n is 1-9; $R^{10}$ is H or an $C_1$-$C_{30}$ alkyl group; $R^1$ is a $R^{10'}$—$N^+(CH_3)_2R^2$; $R^{10'}$ is a $C_2$-$C_{10}$ alkyl; and $R^2$ is a —$(CH_2)_mCH_3$; and m is 0-21.

A cationic alkyl polyglucoside can be, but not limited to, a quaternized polyglucoside, polyquaternized polyglucoside, quaternized alkyl polyglucoside, polyquaternized alkyl polyglucoside, and the like. In some embodiments, the cationic alkyl polyglucoside comprises a single cationic alkyl group having a quaternary ammonium.

In some other embodiments, the cationic alkyl polyglucoside comprises two or more alkyl groups having a quaternary ammonium. In some other embodiments, the cationic alkyl polyglucoside comprises one alkyl group having a quaternary ammonium and one or more nonionic alkyl groups. In yet some other embodiments, the cationic alkyl polyglucoside comprises two or more alkyl groups having a quaternary ammonium and one or more nonionic alkyl groups.

As an example, the cationic alkyl polyglucoside can have a structure of

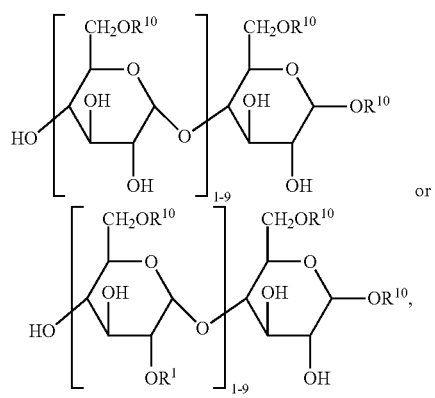

wherein $R^1$ is H or an $C_{10}$-$C_{18}$ alkyl group; $R^{10}$ is a —$CH_2CH(OH)CH_2$—$N^+(CH_3)_2R^2$; and $R^2$ is $C_8$-$C_{18}$ alkyl group. The cationic alkyl polyglucoside can also be

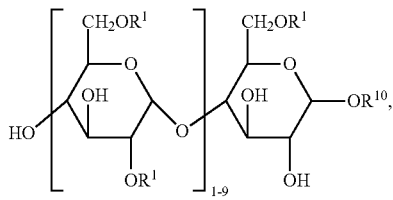

wherein $R^1$ is H or an $C_{10}$-$C_{18}$ alkyl group; $R^{10}$ is a —$CH_2CH(OH)CH_2$—$N^+(CH_3)_2R^2$; and $R^2$ is $C_8$-$C_{18}$ alkyl group. The cationic alkyl polyglucoside can also be

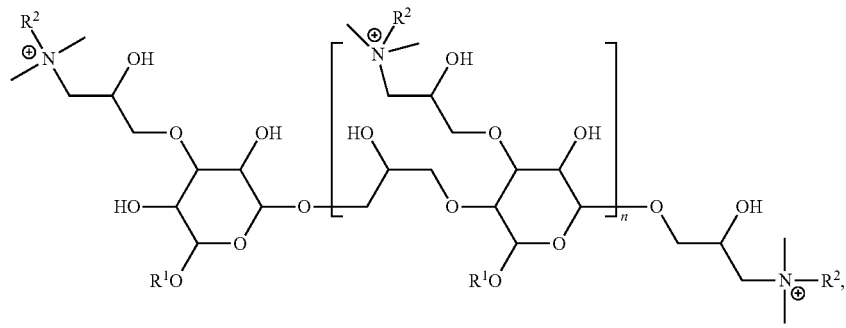

wherein $R^1$ is H or an $C_{10}$-$C_{18}$ alkyl group; $R^2$ is $C_8$-$C_{18}$ alkyl group, and n is 0-10. In some embodiments, the cationic alkyl polyglucoside can also be

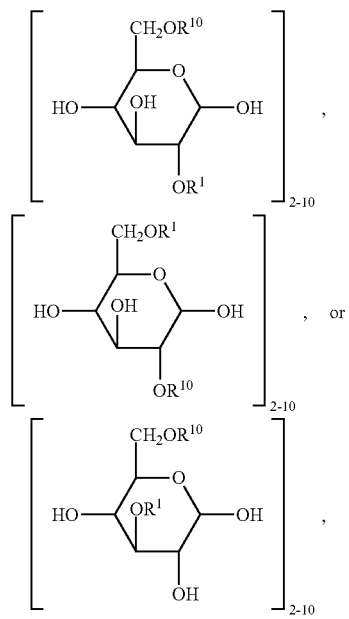

wherein $R^1$ is H or an $C_{10}$-$C_{18}$ alkyl group; $R^{10}$ is a —$(CH_2)_4$—$N^+(CH_3)_2R^2$; and $R^2$ is $C_8$-$C_{18}$ alkyl group.

Examples of commercially suitable cationic alkyl polyglucosides useful in the fouling control compositions disclosed herein can include, but is not limited to, Poly Suga® Quat series of quaternary functionalized alkyl polyglucosides, available from Colonial Chemical, Inc., located in South Pittsburg, Tenn.

Further examples of a suitable quaternary functionalized alkyl polyglucoside include, but are not limited to, the antimicrobial and antifungal quaternary functionalized alkyl polyglucosides described in U.S. Pat. Nos. 7,084,129 and 7,507,399 the disclosures of which are hereby incorporated by reference. Examples of commercially suitable quaternary functionalized alkyl polyglucosides useful in cleansing compositions of the present disclosure can include, but is not limited to, Suga® Quat TM 1212 (primarily $C_{12}$ quaternary functionalized alkyl polyglucoside), Suga® Quat L 1210 (primarily $C_{12}$ quaternary functionalized alkyl polyglucoside), and Suga® Quat S 1218 (primarily $C_{12}$ quaternary functionalized alkyl polyglucoside) available from Colonial Chemical, Inc., located in South Pittsburg, Tenn.

Other Fouling Control Composition Agent in a Fouling Control Composition

In addition to the alkyl polyglycoside, a fouling control composition in the present disclosure includes one or more additional fouling control composition agents.

The additional fouling control composition agent in the disclosed fouling control compositions can include, but is not limited to, an acid, carrier, dispersant, biocide, corrosion inhibitor, antioxidant, polymer degradation prevention agent, permeability modifier, foaming agent, antifoaming agent, fracturing proppant, scavenger for $H_2S$, $CO_2$, and/or $O_2$, gelling agent, lubricant, and friction reducing agent, salt, or mixtures thereof.

The additional fouling control composition agent in the disclosed fouling control compositions can also include, but not be limited to, an organic sulfur compound, asphaltene inhibitor, paraffin inhibitor, scale inhibitor, water clarifier, emulsion breaker, reverse emulsion breaker, gas hydrate inhibitor, a pH modifier, a surfactant, or a combination thereof.

Furthermore, the additional fouling control composition agent can be a sequestrant, solubilizer, lubricant, buffer, cleaning agent, rinse aid, preservative, binder, thickener or other viscosity modifier, processing aid, carrier, water-conditioning agent, or foam generator, threshold agent or system, aesthetic enhancing agent (i.e., dye, odorant, perfume), or other additive suitable for formulation with a reverse emulsion breaker, or mixtures thereof.

The additional fouling control composition agent in a fouling control composition disclosed herein will vary according to the specific fouling control composition being manufactured and its intend use as one skilled in the art will appreciate.

Alternatively, the fouling control composition does not contain or is free of one or more of the additional fouling control composition agents.

When one or more additional fouling control composition agents are used for preventing microbial or biofilm growth, they can be formulated together with the cationic alkyl glucosides as described here in the same fouling control composition. Alternatively, some or all the additional fouling control composition agents can be formulated into one or more different formulations and be supplied to the water system. In other words, the additional fouling control composition agents can be provided into a water system independently, simultaneously, or sequentially.

Biocide and Carrier

In some embodiments, the fouling control compositions disclosed herein further include a biocide. In some other embodiments, the disclosed fouling control compositions herein further include a carrier. In some other embodiments, the disclosed fouling control compositions herein further include a biocide and carrier. In some embodiments, the disclosed methods or fouling control compositions herein may consist of one or more cationic alkyl polyglucosides and carrier. In some embodiments, the fouling control compositions disclosed herein consist of one or more cationic alkyl polyglucosides, a carrier, and biocide.

Biocides suitable for use may be oxidizing or non-oxidizing biocides. Oxidizing biocides include, but are not limited to, bleach, chlorine, bromine, chlorine dioxide, and materials capable of releasing chlorine and bromine. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene(dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis (bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo [2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one.

Suitable non-oxidizing biocides also include, for example, aldehydes (i.e., formaldehyde, glutaraldehyde, and acrolein), amine-type compounds (i.e., quaternary amine compounds and cocodiamine), halogenated compounds (i.e., 2-bromo-2-nitropropane-3-diol (Bronopol) and 2-2-dibromo-3-nitrilopropionamide (DBNPA)), sulfur compounds (i.e., isothiazolone, carbamates, and metronidazole), and quaternary phosphonium salts (i.e., tetrakis(hydroxymethyl)-phosphonium sulfate (THPS)).

Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxycarboxylic acid, peroxycarboxylic acid composition, and peroxides.

The composition can comprise from about 0.1 to about 10 wt-%, from about 0.5 to about 5 wt-%, or from about 0.5 to about 4 wt-% of a biocide, based on total weight of the composition.

A carrier in the disclosed fouling control composition can be water, an organic solvent, or a combination of water and an organic solvent. The organic solvent can be an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The fouling control composition can comprise from about 1 wt-% to about 80 wt-%, from about 1 wt-% to about 70 wt-%, from about 1 wt-% to about 60 wt-%, from about 1 wt-% to about 50 wt-%, from about 1 wt-% to about 40 wt-%, from about 1 wt-% to about 30 wt-%, from about 1 wt-% to about 20 wt-%, from about 1 wt-% to about 10 wt-%, from about 5 wt-% to about 10 wt-%, from about 5 wt-% to about 20 wt-%, from about 5 wt-% to about 30 wt-%, from about 5 wt-% to about 40 wt-%, from about 5 wt-% to about 50 wt-%, from about 10 wt-% to about 20 wt-%, from about 10 wt-% to about 30 wt-%, from about 10 wt-% to about 40 wt-%, from about 10 wt-% to about 50 wt-%, about 10 wt-%, about 20 wt-%, about 30 wt-%, about 40-%, about 50 wt-%, about 60 wt-%, about 70 wt-%, about 90 wt-%, or any value there between of the one or more carrier, based on total weight of the composition.

Corrosion Inhibitor

In some embodiments, the fouling control compositions disclosed herein further include a corrosion inhibitor. In some other embodiments, the disclosed fouling control compositions herein further include a corrosion inhibitor and carrier. In some other embodiments, the disclosed fouling control compositions herein further include a corrosion inhibitor, biocide, and carrier. In some embodiments, the disclosed fouling control compositions herein may consist of one or more cationic alkyl polyglucosides, one or more corrosion inhibitors and carrier. In some embodiments, the fouling control compositions disclosed herein consist of one or more cationic alkyl polyglucosides, a carrier, corrosion inhibitor, and a biocide.

The fouling control composition can comprise from about 0.1 wt-% to about 20 wt-%, from about 0.1 wt-% to about 10 wt-%, or from 0.1 to about 5 wt-% of the one or more corrosion inhibitors, based on total weight of the composition. A composition disclosed herein can comprise from 0 to 10 percent by weight of the one or more corrosion inhibitors, based on total weight of the composition. The composition can comprise about 1.0 wt-%, about 1.5 wt-%, about 2.0 wt-%, about 2.5 wt-%, about 3.0 wt-%, about 3.5 wt-%, about 4.0 wt-%, about 4.5 wt-%, about 5.0 wt-%, about 5.5 wt-%, about 6.0 wt-%, about 6.5 wt-%, about 7.0 wt-%, about 7.5 wt-%, about 8.0 wt-%, about 8.5 wt-%, about 9.0 wt-%, about 9.5 wt-%, about 10.0 wt-%, about 10.5 wt-%, about 11.0 wt-%, about 11.5 wt-%, about 12.0 wt-%, about 12.5 wt-%, about 13.0 wt-%, about 13.5 wt-%, about 14.0 wt-%, about 14.5 wt-%, or about 15.0 wt-% of the one or more corrosion inhibitors, based on total weight of the composition. Each water system can have its own requirements for using a corrosion inhibitor, and the weight percent of one or more corrosion inhibitors in the composition can vary with the water system in which it is used.

A corrosion inhibitor is needed to reduce corrosion of metals in the water system. Corrosion inhibitors for multi-metal protection are typically triazoles, such as, but not limited to, benzotriazole, halogenated triazoles, and nitro-substituted azoles.

The one or more corrosion inhibitors can be an imidazoline compound, a quaternary ammonium compound, a pyridinium compound, or a combination thereof.

The one or more corrosion inhibitors can be an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (1A) or an imidazoline derivative. Representative imidazoline derivatives include an imidazolinium compound of Formula (2A) or a bis-quaternized compound of Formula (3A).

The one or more corrosion inhibitors can include an imidazoline of Formula (1A):

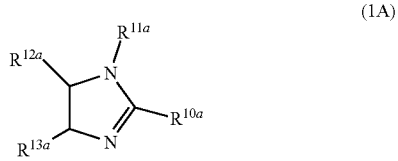

(1A)

wherein $R^{10a}$ is a $C_1$-$C_{20}$ alkyl or a $C_1$-$C_{20}$ alkoxyalkyl group; $R^{11a}$ is hydrogen, $C_1$-$C_6$ alkyl, $C_1$-$C_6$ hydroxyalkyl, or $C_1$-$C_6$ arylalkyl; and $R^{12a}$ and $R^{13a}$ are independently hydrogen or a $C_1$-$C_6$ alkyl group. Preferably, the imidazoline includes an $R^{10a}$ which is the alkyl mixture typical in tall oil fatty acid (TOFA), and $R^{11a}$, $R^{12a}$ and $R^{13a}$ are each hydrogen.

The one or more additional corrosion inhibitors can be an imidazolinium compound of Formula (2A):

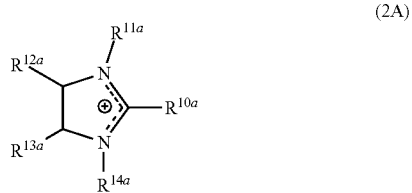

(2A)

wherein $R^{10a}$ is a $C_1$-$C_{20}$ alkyl or a $C_1$-$C_{20}$ alkoxyalkyl group; $R^{11a}$ and $R^{14a}$ are independently hydrogen, $C_1$-$C_6$ alkyl, $C_1$-$C_6$ hydroxyalkyl, or $C_1$-$C_6$ arylalkyl; $R^{12a}$ and $R^{13a}$ are independently hydrogen or a $C_1$-$C_6$ alkyl group; and X⁻ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can be a bis-quaternized compound having the formula (3A):

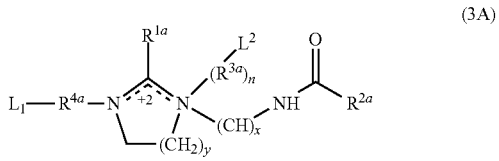

(3A)

wherein $R^{1a}$ and $R^{2a}$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R^{3a}$ and $R^{4a}$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO₃H, —PO₃H, —COOR$^{5a}$, —CONH₂, —CONHR$^{5a}$, or —CON(R$^{5a}$)₂; $R^{5a}$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R^{1a}$ and $R^{2a}$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R^{3a}$ and $R^{4a}$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C₂H₂—; $L_1$ is —COOH, —SO₃H, or —PO₃H; and $L_2$ is absent, H, —COOH, —SO₃H, or —PO₃H. For example, $R^{1a}$ and $R^{2a}$ can be derived from a mixture of tall oil fatty acids and are predominantly a mixture of $C_{17}H_{33}$ and $C_{17}H_{31}$ or can be $C_{16}$-$C_{18}$ alkyl; $R^{3a}$ and $R^{4a}$ can be $C_2$-$C_3$ alkylene such as —C₂H₂—; n is 1 and $L_2$ is —COOH or n is 0 and $L_2$ is absent or H; x is 2; y is 1; $R^{3a}$ and $R^{4a}$ are —C₂H₂—; and $L_1$ is —COOH.

It should be appreciated that the number of carbon atoms specified for each group of formula (3A) refers to the main chain of carbon atoms and does not include carbon atoms that may be contributed by substituents.

The one or more corrosion inhibitors can be a bis-quaternized imidazoline compound having the formula (3A) wherein $R^{1a}$ and $R^{2a}$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R^{4a}$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO₃H, or —PO₃H; and $L_2$ is absent or H. Preferably, a bis-quaternized compound has the formula (3A) wherein $R^{1a}$ and $R^{2a}$ are each independently $C_{16}$-$C_{18}$ alkyl; $R^{4a}$ is —C₂H₂—; x is 2; y is 1; n is 0; $L_1$ is —COOH, —SO₃H, or —PO₃H and $L_2$ is absent or H.

The one or more corrosion inhibitors can be a quaternary ammonium compound of Formula (4A):

(4A)

wherein $R^{1a}$, $R^{2a}$, and $R^{3a}$ are independently $C_1$ to $C_{20}$ alkyl, $R^{4a}$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I. For the quaternary salts, $R^{5a}$, $R^{6a}$, $R^{7a}$, $R^{8a}$ can each be independently alkyl (i.e., $C_1$-$C_{18}$ alkyl), hydroxyalkyl (i.e., $C_1$-$C_{18}$ hydroxyalkyl), and arylalkyl (i.e., benzyl). The mono or polycyclic aromatic amine salt with an alkyl or alkylaryl halide include salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more corrosion inhibitors can be a pyridinium salt such as those represented by Formula (5A):

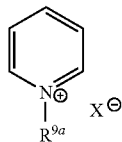

(5A)

wherein $R^{9a}$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitors can be a phosphate ester, monomeric or oligomeric fatty acid, alkoxylated amine, or mixture thereof.

The one or more corrosion inhibitors can be a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a broader distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more corrosion inhibitors can be a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more corrosion inhibitors can be an alkoxylated amine. The alkoxylated amine can be an ethoxylated alkyl amine. The alkoxylated amine can be ethoxylated tallow amine.

Dispersant

In some embodiments, the fouling control compositions disclosed herein can further comprise a dispersant. A dispersant keeps particulate matter present in the water of a water system dispersed, so that it does not agglomerate. The composition can comprise from about 0.1 to 10 wt-%, from about 0.5 to 5 wt-%, or from about 0.5 to 4 wt-% of a dispersant, based on total weight of the composition.

A dispersant may be an acrylic acid polymer, maleic acid polymer, copolymer of acrylic acid with sulfonated monomers, alkyl esters thereof, or combination thereof. These polymers may include terpolymers of acrylic acid, acrylamide and sulfonated monomers. These polymers may also include quad-polymers consisting of acrylic acid and three other monomers.

Suitable dispersants include, but are not limited to, aliphatic phosphonic acids with 2-50 carbons, such as hydroxyethyl diphosphonic acid, and aminoalkyl phosphonic acids, i.e. polyaminomethylene phosphonates with 2-10 N atoms i.e. each bearing at least one methylene phosphonic acid group; examples of the latter are ethylenediamine tetra(methylene phosphonate), diethylenetriamine penta(m-ethylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The fouling control composition can further comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. Such compounds are used as synergists in the composition. The organic sulfur compound can constitute from about 0.5 wt-% to about 15 wt-% of the composition, based on total weight of the composition, preferably from about 1 wt-% to about 10 wt-% and more preferably from about 1 wt-% to about 5 wt-%. The organic sulfur compound can constitute about 1 wt-%, about 2 wt-%, about 3 wt-%, about 4 wt-%, about 5 wt-%, about 6 wt-%, about 7 wt-%, about 8 wt-%, about 9 wt-%, about 10 wt-%, about 11 wt-%, about 12 wt-%, about 13 wt-%, about 14 wt-%, or about 15 wt-% of the composition.

The fouling control composition can further comprise a de-emulsifier. Preferably, the demulsifier comprises an oxyalkylate polymer, such as a polyalkylene glycol. The de-emulsifier can constitute from about 0.1 wt-% to about 10 wt-%, from about 0.5 wt-% to about 5 wt. %, or from about 0.5 wt-% to about 4 wt-% of the composition, based on total weight of the composition. The de-emulsifier can constitute about 0.5 wt-%, about 1 wt-%, about 1.5 wt-%, about 2 wt-%, about 2.5 wt-%, about 3 wt-%, about 3.5 wt-%, about 4 wt-%, about 4.5 wt-%, or about 5 wt-% of the composition.

The fouling control composition can further comprise an asphaltene inhibitor. The composition can comprise from about 0.1 wt-% to about 10 wt-%, from about 0.1 wt-% to about 5 wt-%, or from about 0.5 wt-% to about 4 wt-% of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The fouling control composition can further comprise a paraffin inhibitor. The composition can comprise from about 0.1 wt-% to about 10 wt-%, from about 0.1 wt-% to about 5 wt-%, or from about 0.5 wt-% to about 4 wt-% of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The fouling control composition can further comprise a scale inhibitor. The composition can comprise from about 0.1 wt-% to about 20 wt-%, from about 0.5 wt-% to about 10 wt-%, or from about 1 wt-% to about 5 wt-% of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), mono-, bis- and oligomeric phosphinosuccinic acid (PSO) derivatives, polycarboxylic acid, hydrophobically modified polycarboxylic acid, and salts of a polymaleic acid/acrylic acid/acrylamidomethyl propane sulfonate terpolymer (PMA/AA/AMPS).

The fouling control composition can further comprise an emulsifier. The composition can comprise from about 0.1 wt-% to about 10 wt-%, from about 0.5 wt-% to about 5 wt-%, or from about 0.5 wt-% to about 4 wt-% of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The fouling control composition can further comprise a water clarifier. The composition can comprise from about 0.1 wt-% to about 10 wt-%, from about 0.5 wt-% to about 5 wt-%, or from about 0.5 wt-% to about 4 wt-% of a water clarifier, based on total weight of the composition. Suitable water clarifiers include, but are not limited to, inorganic metal salts such as alum, aluminum chloride, and aluminum chlorohydrate, or organic polymers such as acrylic acid-based polymers, acrylamide-based polymers, polymerized amines, alkanolamines, thiocarbamates, and cationic polymers such as diallyldimethylammonium chloride (DADMAC).

The fouling control composition can further comprise an emulsion breaker. The composition can comprise from about 0.1 wt-% to about 10 wt-%, from about 0.5 wt-% to about 5 wt-%, or from about 0.5 wt-% to about 4 wt-% of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, and resins, such as phenolic and epoxide resins.

The fouling control composition can further comprise a hydrogen sulfide scavenger. The composition can comprise from about 1 wt-% to about 50 wt-%, from about 1 wt-% to about 40 wt-%, from about 1 wt-% to about 30 wt-%, from about 0.1 wt-% to about 10 wt-%, from about 0.5 wt-% to about 5 wt-%, or from about 0.5 wt-% to about 4 wt-% of a hydrogen sulfide scavenger, based on total weight of the composition. Suitable additional hydrogen sulfide scavengers include, but are not limited to, oxidants (i.e., inorganic peroxides such as sodium peroxide or chlorine dioxide); aldehydes (i.e., of 1-10 carbons such as formaldehyde, glyoxal, glutaraldehyde, acrolein, or methacrolein; triazines (i.e., monoethanolamine triazine, monomethylamine triazine, and triazines from multiple amines or mixtures thereof); condensation products of secondary or tertiary amines and aldehydes, and condensation products of alkyl alcohols and aldehydes.

The fouling control composition can further comprise a gas hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (i.e. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (i.e. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The fouling control composition can further comprise a kinetic hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines, hydrocarbon based dispersants (such as lignosulfonates, iminodisuccinates, polyaspartates), amino acids, and proteins.

The fouling control composition can further comprise a pH modifier. The composition can comprise from about 0.1 wt-% to about 20 wt-%, from about 0.5 wt-% to about 10 wt-%, or from about 0.5 wt-% to about 5 wt-% of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The fouling control composition can further comprise a surfactant. The composition can comprise from about 0.1 wt-% to about 10 wt-%, from about 0.5 wt-% to about 5 wt-%, or from about 0.5 wt-% to about 4 wt-% of a surfactant, based on total weight of the composition. A suitable surfactant can be a nonionic, semi-nonionic, cationic, anionic, amphoteric, zwitterionic, Gemini, di-cationic, di-anionic surfactant, or mixtures thereof. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

The fouling control composition can further comprise additional fouling control composition agents that provide a functional and/or beneficial property. For example, additional fouling control composition agents can be a sequestrant, solubilizer, lubricant, buffer, cleaning agent, rinse aid, preservative, binder, thickener or other viscosity modifier, processing aid, water-conditioning agent, foam inhibitor or foam generator, threshold agent or system, aesthetic enhancing agent (i.e., dye, odorant, perfume), or other agents suitable for formulation with the fouling control composition, and mixtures thereof. Additional agents or additives will vary according to the specific fouling control composition being manufactured and its intend use as one skilled in the art will appreciate.

Alternatively, the fouling control composition does not contain or is free of any of the additional fouling control composition agents.

Additionally, the fouling control composition can be formulated into compositions comprising the following components as shown in Table 1. These formulations include the ranges of the components listed and can optionally include additional agents. The values in the Table 1 below are weight percentages.

TABLE 1

Exemplary Fouling Control Compositions

| Component | 1 | 2 | 3 | 4 | 5 | 6 | 7 | 8 | 9 | 10 | 11 | 12 |
|---|---|---|---|---|---|---|---|---|---|---|---|---|
| Cationic Alkyl Polyglucoside | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Surfactant | 5-40 | — | 5-50 | — | 5-50 | 5-50 | 5-40 | — | 5-50 | — | — | 10-20 |
| corrosion inhibitor | 0.1-20 | 0.1-20 | — | — | — | — | 0.1-20 | 0.1-20 | — | — | — | 0.1-20 |
| Preservative | 0.1-5 | 0.1-5 | 0.1-5 | 0.1-5 | — | — | 0.1-5 | 0.1-5 | 0.1-5 | — | — | 0.1-5 |
| Scale inhibitor | 1-10 | 1-10 | 1-10 | 1-10 | 1-10 | — | 1-10 | 1-10 | 1-10 | 1-10 | — | 1-10 |
| Water Clarifier | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| Water | 0.00 | 0-40 | 1-10 | 0-60 | 0-15 | 0-25 | 0.00 | 0-40 | 1-10 | 0-65 | 0-75 | |

| Component | 13 | 14 | 15 | 16 | 17 | 18 | 19 | 20 | 21 | 22 | 23 | 24 |
|---|---|---|---|---|---|---|---|---|---|---|---|---|
| Cationic Alkyl Polyglucoside | 0.1-20 | 0.1-20 | 0.1-20 | 0.1-20 | 0.1-20 | 0.1-20 | 10-20 | 10-20 | 10-20 | 10-20 | 10-20 | 10-20 |
| Surfactant | — | 10-20 | — | 10-35 | 10-35 | — | 10-15 | — | — | 10-35 | 10-35 | — |
| Corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Preservative | 0.1-5 | — | — | — | — | — | 0.1-5 | — | — | — | — | — |
| Scale inhibitor | 1-10 | 1-10 | — | — | 1-10 | — | 1-10 | 1-10 | — | — | — | 1-10 |
| Water Clarifier | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 |

Water System

In some embodiments, the water system in the disclosed methods herein is an industrial water system. In other embodiments, the water system can be, but is not limited to, a cooling water system, including an open recirculating system, closed and once-through cooling water system, boilers and boiler water system, petroleum well system, downhole formation, geothermal well, and other water system in oil and gas field applications, a mineral washing system, flotation and benefaction system, paper mill digester, washer, bleach plant, stock chest, white water system, paper machine surface, black liquor evaporator in the pulp industry, gas scrubber and air washer, continuous casting processes in the metallurgical industry, air conditioning and refrigeration system, industrial and petroleum process water, indirect contact cooling and heating water, water reclamation system, water purification system, membrane filtration water system, food processing stream (meat, vegetable, sugar beets, sugar cane, grain, poultry, fruit and soybean), waste treatment system, clarifier, liquid-solid application, municipal sewage treatment, municipal water system, potable water system, aquifer, water tank, sprinkler system, or water heater.

In some embodiments, the water system is a cooling water system, including open recirculating, closed and once-through cooling water system, paper machine surface, food processing stream, waste treatment system, or potable water system.

In some embodiments, the water system is any system including a wetable surface. Examples of such water systems include, but are not limited to, walls and floors of bath rooms, surfaces of foods and vegetables, and processing fluid for food. Such surfaces are typically in constant contact with water or water moisture and subjected to biofilm growth.

Use of the Methods or Compositions Disclosed

In some embodiments, for the methods disclosed herein, providing a fouling control composition into a water system means that the fouling control composition or cationic alkyl polyglucosides are added into a fluid comprising water or surfaces of a water system. In other embodiments, providing a fouling control composition into a water system means adding the fouling control composition or cationic alkyl polyglucosides to the surface or water of the water system. In some other embodiments, providing a fouling control composition into a water system means adding the fouling control composition or cationic alkyl polyglucosides to a fluid or gas which contacts the surfaces of the water system. The fouling control composition or cationic alkyl polyglucosides may be added continuously, or intermittently when more compounds or compositions may be needed.

In some embodiments, the fouling control composition or cationic alkyl polyglucosides may be added to the water of the water system in an amount ranging from about 1 ppm to about 1000 ppm. In other embodiments, the amount of the fouling control composition or cationic alkyl polyglucosides in the water of the water system may range from about 5 ppm to about 100 ppm, from about 5 ppm to about 50 ppm, from about 5 ppm to about 40 ppm, from about 5 ppm to about 30 ppm, from about 10 ppm to about 60 ppm, from about 10 ppm to about 50 ppm, from about 10 ppm to about 40 ppm, from about 10 ppm to about 30 ppm, from about 20 ppm to about 60 ppm, from about 20 ppm to about 50 ppm, from about 20 ppm to about 40 ppm, or from about 20 ppm to about 30 ppm. In some embodiments, the fouling control composition or cationic alkyl polyglucosides may be added to the water to an amount ranging from about 100 ppm to about 1000 ppm, from about 125 ppm to about 1000 ppm, from about 250 ppm to about 1000 ppm, or from about 500 ppm to about 1000 ppm in the treated water system.

The fouling control composition or cationic alkyl polyglucosides can be used for fouling control in oil and gas applications such as by treating a gas or liquid stream with an effective amount of the compound or composition as described herein. The compounds and compositions can be used in any industry where it is desirable to prevent microbial or biofilm growth at a surface.

The fouling control composition or cationic alkyl polyglucosides can be used in a condensate/oil systems/gas system, or any combination thereof. For example, the fouling control composition or cationic alkyl polyglucosides can be used in fouling control on heat exchanger surfaces. The fouling control composition or cationic alkyl polyglucosides can be applied to a gas or liquid produced, or used in the production, transportation, storage, and/or separation of crude oil or natural gas. The fouling control composition or cationic alkyl polyglucosides can be applied to a gas stream used or produced in a coal-fired process, such as a coal-fired power plant.

The fouling control composition or cationic alkyl polyglucosides can be applied to a gas or liquid produced or used in a waste-water process, a farm, a slaughter house, a land-fill, a municipality waste-water plant, a coking coal process, or a biofuel process.

A fluid to which the fouling control composition or cationic alkyl polyglucosides can be introduced can be an aqueous medium. The aqueous medium can comprise water, gas, and optionally liquid hydrocarbon.

A fluid to which the fouling control composition or cationic alkyl polyglucosides can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with the fouling control composition or cationic alkyl polyglucosides can be at any selected temperature, such as ambient temperature or an elevated temperature. The fluid (e.g., liquid hydrocarbon) or gas can be at a temperature of from about 40° C. to about 250° C. The fluid or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The fouling control composition or cationic alkyl polyglucosides can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the fouling control composition or cationic alkyl polyglucosides are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The fouling control composition or cationic alkyl polyglucosides can be introduced into a fluid or gas of the water system by any appropriate method for ensuring dispersal through the fluid or gas. For examples, the fouling control composition or cationic alkyl polyglucosides can be added to the hydrocarbon fluid before the hydrocarbon fluid contacts the surface.

The fouling control composition or cationic alkyl polyglucosides can be added at a point in a flow line upstream from the point at which fouling control is desired. The fouling control composition or cationic alkyl polyglucosides can be injected using mechanical equipment such as chemical injection pumps, piping tees, injection fittings, atomizers, quills, and the like.

The fouling control composition or cationic alkyl polyglucosides can be pumped into an oil and/or gas pipeline using an umbilical line. A capillary injection system can be used to deliver the fouling control composition or cationic alkyl polyglucosides to a selected fluid.

A fluid to which the fouling control composition or cationic alkyl polyglucosides can be introduced can be an aqueous medium. The aqueous medium can comprise water, gas, and optionally liquid hydrocarbon. A fluid to the fouling control composition or cationic alkyl polyglucosides can be introduced can be a liquid hydrocarbon.

The fouling control composition or cationic alkyl polyglucosides can be introduced into a liquid and a mixture of several liquids, a liquid and gas, liquid, solid, and gas. The fouling control composition or cationic alkyl polyglucosides can be injected into a gas stream as an aqueous or non-aqueous solution, mixture, or slurry.

The fluid or gas can be passed through an absorption tower comprising the fouling control composition or cationic alkyl polyglucosides.

The fouling control composition or cationic alkyl polyglucosides can be applied to a fluid or gas to provide any selected concentration. In practice, the fouling control composition or cationic alkyl polyglucosides are typically added to a flow line to provide an effective treating dose of the fouling control composition or cationic alkyl polyglucosides from about 0.01 to about 5,000 ppm. The fouling control composition or cationic alkyl polyglucosides can be applied to a fluid or gas to provide an active concentration of about 1 parts per million (ppm) to about 1,000,000 ppm, about 1 parts per million (ppm) to about 100,000 ppm, or from about 10 ppm to about 75,000 ppm. The cationic alkyl polyglycoside/compositions can be applied to a fluid to provide an actives concentration of from about 100 ppm to about 10,000 ppm, from about 200 ppm to about 8,000 ppm, or from about 500 ppm to about 6,000 ppm. The actives concentration means the concentration of fouling control composition or cationic alkyl polyglucosides.

The fouling control composition or cationic alkyl polyglucosides can be applied to a fluid or gas to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm. The polymer salts/compositions can be applied to a fluid or gas to provide an actives concentration of about 0.125 ppm, about 0.25 ppm, about 0.625 ppm, about 1 ppm, about 1.25 ppm, about 2.5 ppm, about 5 ppm, about 10 ppm, or about 20 ppm in the treated fluid, gas, or water system. Each water system can have its own dose level requirements, and the effective dose level of the fouling control composition or cationic alkyl polyglucosides to sufficiently reduce the rate of microbial or biofilm growth can vary with the water system in which it is used.

The fouling control composition or cationic alkyl polyglucosides can be applied continuously, in batch, or a combination thereof. The fouling control composition or cationic alkyl polyglucosides dosing can be continuous. The fouling control composition or cationic alkyl polyglucosides dosing can be intermittent (e.g., batch treatment) or can be continuous/maintained and/or intermittent.

Dosage rates for continuous treatments typically range from about 10 to about 500 ppm, or from about 10 ppm to about 200 ppm. Dosage rates for batch treatments typically range from about 10 ppm to about 400,000 ppm, or from about 10 ppm to about 20,000 ppm. The fouling control composition or cationic alkyl polyglucosides can be applied as a pill to a pipeline, providing a high dose (e.g., 20,000 ppm) of the composition.

The flow rate of a flow line in which the fouling control composition or cationic alkyl polyglucosides is used can be between about 0.1 feet per second and about 100 feet per second, or between about 0.1 feet per second and about 50 feet per second. The fouling control composition or cationic alkyl polyglucosides can also be formulated with water to facilitate addition to the flow line.

The surface can be a part of a wellbore or equipment used in the production, transportation, storage, and/or separation of a fluid such as crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The equipment can comprise a pipeline, a storage vessel, downhole injection tubing, a flow line, or an injection line.

The fouling control composition or cationic alkyl polyglucosides are useful for corrosion inhibition of containers, processing facilities, or equipment in the food service or food processing industries. The fouling control composition or cationic alkyl polyglucosides have particular value for use on food packaging materials and equipment, and especially for cold or hot aseptic packaging. Examples of process facilities in which the fouling control composition or cationic alkyl polyglucosides can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The fouling control composition or cationic alkyl polyglucosides can be used to inhibit corrosion in tanks, lines, pumps, and other equipment used for the manufacture and storage of soft drink materials, and also used in the bottling or containers for the beverages.

The fouling control composition or cationic alkyl polyglucosides can also be used on or in other industrial equipment and in other industrial process streams such as heaters, cooling towers, boilers, retort waters, rinse waters, aseptic packaging wash waters, and the like. The fouling control composition or cationic alkyl polyglucosides can be used to treat surfaces in recreational waters such as in pools, spas, recreational flumes and water slides, fountains, and the like.

The fouling control composition or cationic alkyl polyglucosides can be used to treat surfaces contacted with cleaners in surfaces found in janitorial and/or housekeeping applications, food processing equipment and/or plant applications, and in laundry applications. For example, washers, such as tunnel washers for washing textiles, can be treated according to methods disclosed herein.

The fouling control composition or cationic alkyl polyglucosides can be used or applied in combination with low temperature dish and/or ware wash sanitizing final rinse, toilet bowl cleaners, and laundry bleaches. The fouling control composition or cationic alkyl polyglucosides can be used to treat metal surfaces, such as ware, cleaned and/or sanitized with corrosive sources.

The fouling control composition or cationic alkyl polyglucosides can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The fouling control composition or cationic alkyl polyglucosides can be dispensed by immersing either intermittently or continuously in the water, fluid, or gas of the water system. The fouling control composition or cationic alkyl polyglucosides can then dissolve, for example, at a controlled or predetermined rate. The rate can be effective to maintain a concentration of the dissolved compounds or compositions that are effective for use according to the methods disclosed herein.

The fouling control composition disclosed herein can comprise from about 10 to about 90 wt-% of the carrier, biocide, corrosion inhibitor, additional fouling control composition agent, a combination thereof and from about 10 wt-% to about 90 wt-% of one or more cationic alkyl polyglucosides; from about 20 wt-% to about 80 wt-% of the carrier, biocide, corrosion inhibitor, additional fouling control composition agent, a combination thereof and from about 10 wt-% to about 80 wt-% of one or more cationic alkyl polyglucosides, from about 30 wt-% to about 70 wt-% of the carrier, biocide, corrosion inhibitor, additional fouling control composition agent, or a combination thereof and from about 30 wt-% to about 70 wt-% of one or more cationic alkyl polyglucosides, or from about 40 wt-% to about 60 wt-% of the carrier, biocide, corrosion inhibitor, additional fouling control composition agent, or a combination thereof and from about 70 wt-% to about 84 wt. % of one or more cationic alkyl polyglucosides.

In one aspect, disclosed herein is a fouling control composition for a water system, wherein the fouling control composition comprises a cationic alkyl polyglucoside and one or more additional fouling control composition agents, wherein the fouling control composition reduces bacterial growth or biofilm growth in the water system.

In another aspect, disclosed herein is a method of controlling microbial fouling in a water system, wherein the method comprises providing a fouling control composition into a water system to generate a treated water system, wherein the fouling control composition comprises a cationic alkyl polyglucoside and wherein the fouling control composition reduces bacterial growth or biofilm growth in the water system.

In some embodiments, the fouling control composition further comprises one or more additional fouling control composition agents.

In some embodiments, the cationic alkyl polyglycoside is a cationic alkyl polyglucoside.

In some embodiments, the cationic alkyl polyglucoside comprises one or more glucose units and at least one cationic alkyl group R—Y, wherein R is an alkyl group and Y is a cationic group. In some other embodiments, the cationic alkyl polyglucoside is one of

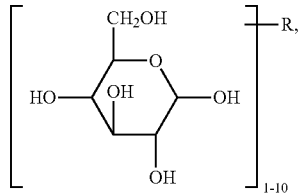

wherein R is an alkyl group; R is attached to at least one, more than one, or all of the OH groups; and at least one R group contains a cationic group Y.

In some embodiments, the cationic alkyl polyglucoside comprises two or more glucose units and the glucose units are connected by glycosidic bond. In some other embodiments, the cationic alkyl polyglucoside comprises two or more glucose units and the glucose units are connected by a non-glycosidic bond. In yet some other embodiments, the cationic alkyl polyglucoside comprises two or more glucose units and the glucose units are connected through a linker. In some other embodiments, the cationic alkyl polyglucoside comprises three or more glucose units and the glucose units are connected through a linker, glycosidic bond, non-glycosidic bond, or combination thereof.

In some embodiments, R is a $C_1$-$C_{30}$ alkyl. In some other embodiments, R is $C_8$-$C_{24}$ alkyl.

In some embodiments, the cationic group Y is —$NR^4R^5R^{6(+)}$, and $R^4$, $R^5$, and $R^6$ are independently $CH_3$. In some other embodiments, the cationic group Y is —$NR^4R^5R^{6(+)}$, $R^4$ and $R^5$ are independently $CH_3$, and $R^6$ is a $C_2$-$C_{12}$ aromatic alkyl. In yet some other embodiments, the cationic group Y is —$NR^4R^5R^{6(+)}$, $R^4$ and $R^5$ are independently $CH_3$, and $R^6$ is —$CH_2$—$C_6H_6$.

In some embodiments, the cationic group Y is —$NR^4R^5R^{6(+)}$ and the counter ion for the cationic group Y is chloride, bromide, fluoride, iodide, acetate, aluminate, cyanate, cyanide, dihydrogen phosphate, dihydrogen phosphite, formate, hydrogen carbonate, hydrogen oxalate, hydrogen sulfate, hydroxide, nitrate, nitrite, thiocyanate, or a combination thereof.

In some embodiments, the cationic alkyl polyglucoside comprises one cationic alkyl group R—Y. In some other embodiments, wherein the cationic alkyl polyglucoside comprises two same or different cationic alkyl groups R—Y.

In yet some other embodiments, the cationic alkyl polyglucoside comprises three or more same or different cationic alkyl groups R—Y.

In some embodiments, the cationic alkyl polyglucoside further comprises one or more nonionic same or different alkyl groups $R^3$. In some other embodiments, $R^3$ is an unsubstituted, linear, and saturated $C_1$-$C_{20}$ alkylene group. In yet some other embodiments, $R^3$ is an unsubstituted, linear, and unsaturated $C_1$-$C_{20}$ alkylene group. In some other embodiments, $R^3$ is a linear $C_8$-$C_{18}$ alkyl, alkenyl, or alkynyl group. In some other embodiments, $R^3$ is a branched $C_8$-$C_{20}$ alkyl, alkenyl, or alkynyl group.

In some embodiments, the cationic alkyl polyglucoside is a single compound. In some other embodiments, the cationic alkyl polyglucoside is a mixture of two or more different alkyl polyglucosides, wherein the two or more different alkyl polyglucosides differ from each other by molecular weight, structure, net charge, or combination thereof.

In some embodiments, the cationic alkyl polyglucoside has an average molecular weight of from about 200 to about 5,500 Da.

In some embodiments, the cationic alkyl polyglucoside is propanol, isopropanol, butanol, isobutanol, monoethyleneglycol, ethyleneglycol monobutyl ether, or a combination thereof.

In some embodiments, the organic solvent is methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, a mixture thereof with water, or any combination thereof.

In some embodiments, wherein the fouling control composition further comprises one or more of corrosion inhibitors. In some embodiments, wherein the fouling control composition further comprises one or more of corrosion inhibitors and a carrier. In some embodiments, the corrosion inhibitor is an imidazoline compound, a pyridinium compound, or a combination thereof.

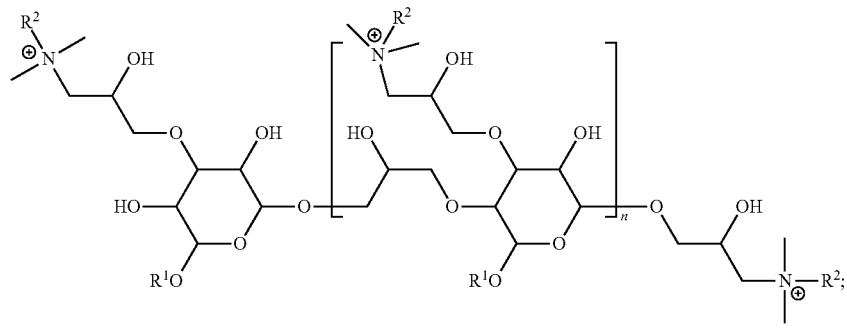

wherein n is 0-10, $R^1$ is a $C_1$-$C_{30}$ alkyl, and $R^2$ is a $C_1$-$C_{30}$ alkyl. In some embodiments, n is 0. In some other embodiments, n is 1. In yet some other embodiments, n is 2. In some embodiments, n is 3, 4, 5, 6, 7, 8, 9, or 10. In some embodiments, the cationic alkyl polyglycoside is a mixture of the polyglucosides as shown above with different n values.

In some embodiments, $R^1$ is a $C_6$-$C_{20}$ alkyl. In some other embodiments, $R^1$ is a $C_8$-$C_{18}$ alkyl. In yet some other embodiments, $R^2$ is a $C_6$-$C_{20}$ alkyl. In some other embodiments, $R^2$ is a $C_8$-$C_{18}$ alkyl.

In some embodiments, $R^2$ and $R^1$ are $C_8$-$C_{18}$ alkyls.

In some embodiments, the alkyl polyglucoside is soluble or dispersible in water or the fouling control composition.

In some embodiments, the fouling control composition comprises a carrier, wherein the carrier is water, an organic solvent, or a mixture thereof.

In some embodiments, the fouling control composition further comprises an organic solvent. In some other embodiments, the fouling control composition further comprises an organic solvent and water.

In some embodiments, the organic solvent is an alcohol, a hydrocarbon, a ketone, an ether, an alkylene glycol, a glycol ether, an amide, a nitrile, a sulfoxide, an ester, or any combination thereof. In some other embodiments, the organic solvent is an alcohol, an alkylene glycol, an alkyleneglycol alkyl ether, or a combination thereof. In yet some embodiments, the organic solvent is methanol, ethanol, In some embodiments, the fouling control composition further comprises an additional fouling control composition agent. In some embodiments, the additional fouling control composition agent is a single quaternary compound.

In some embodiments, the fouling control composition further comprises a biocide. In some embodiments, the fouling control composition further comprises a biocide and carrier. In some other embodiments, the fouling control composition further comprises a biocide, corrosion inhibitor, and carrier.

In some other embodiments, the biocide is chlorine, hypochlorite, $ClO_2$, bromine, ozone, hydrogen peroxide, peracetic acid, peroxycarboxylic acid, peroxycarboxylic acid composition, peroxysulphate, glutaraldehyde, dibromonitrilopropionamide, isothiazolone, terbutylazine, polymeric biguanide, methylene bisthiocyanate, tetrakis hydroxymethyl phosphonium sulphate, and any combination thereof.

In some embodiments, the fouling control composition further comprises an organic sulfur compound. In some other embodiments, wherein the organic sulfur compound is a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof.

In some embodiments, the fouling control composition further comprises an acid. In some embodiments, the fouling control composition further comprises an inorganic acid, mineral acid, organic acid, or mixture thereof. In some embodiments, the fouling control composition comprises from about 1 wt-% to about 20 wt-% of the acid.

In some embodiments, the acid is hydrochloric acid, hydrofluoric acid, citric acid, formic acid, acetic acid, or mixture thereof.

In some embodiments, the fouling control composition further comprises a hydrogen sulfide scavenger. In some other embodiments, the hydrogen sulfide scavenger is an oxidant, inorganic peroxide, sodium peroxide, chlorine dioxide; a $C_1$-$C_{10}$ aldehyde, formaldehyde, glyoxal, glutaraldehyde, acrolein, or methacrolein, a triazine, monoethanolamine triazine, monomethylamine triazine, or a mixture thereof.

In some embodiments, the fouling control composition further comprises a surfactant. In some embodiments, the fouling control composition further comprises a surfactant, biocide, and carrier.

In some embodiments, the surfactant is a nonionic, cationic, anionic, amphoteric, zwitterionic, Gemini, di-cationic, di-anionic surfactant, or mixtures thereof.

In some embodiments, the surfactant is an alkyl phenol, fatty acid, or mixture thereof.

In some embodiments, the fouling control composition further comprises an asphaltene inhibitor, a paraffin inhibitor, a scale inhibitor, a gas hydrate inhibitor, a pH modifier, or any combination thereof.

In some embodiments, the fouling control composition further comprises an emulsion breaker, reverse emulsion breaker, coagulant/flocculant agent, an emulsifier, a water clarifier, a dispersant, antioxidant, polymer degradation prevention agent, permeability modifier, foaming agent, antifoaming agent, emulsifying agent, scavenger agent for $CO_2$, and/or $O_2$, gelling agent, lubricant, friction reducing agent, salt, or mixture thereof.

In some embodiments, the fouling control composition further comprises a surfactant. In some other embodiments, the fouling control composition further comprises a foaming surfactant. In yet some other embodiments, the fouling control composition further comprises a defoaming surfactant or agent.

In some embodiments, the fouling control composition further comprises a preservative. In some other embodiments, the fouling control composition further comprises a non-oxidizing biocide, surfactant, biocide, and preservative. In yet some other embodiments, the fouling control composition further comprises a non-oxidizing biocide, surfactant, biocide, preservative and water clarifier. In some other embodiments, the fouling control composition further comprises a surfactant, biocide, preservative, and water clarifier.

In some embodiments, the fouling control composition is a liquid, gel, or a mixture comprising liquid/gel and solid.

In some embodiments, the fouling control composition or a use solution thereof has a pH of from about 2 to about 11.

In some embodiments, the fouling control composition comprises from about 20 wt-% to about 60 wt-% of the alkyl glucoside or a mixture thereof.

In some embodiments, the alkyl polyglucoside or mixture thereof has a concentration of from about 1 ppm to about 1000 ppm in the treated water system.

In some embodiments, the fouling control composition is provided to the water system independently, simultaneously, or sequentially with an additional functional ingredient.

In some embodiments, the water system comprises fresh water, recycled water, salt water, surface water, produced water, or mixture thereof. In some embodiments, the water system is a cooling water system, boiler water system, petroleum wells, downhole formations, geothermal wells, mineral washing, flotation and benefaction, papermaking, gas scrubbers, air washers, continuous casting processes in the metallurgical industry, air conditioning and refrigeration, water reclamation, water purification, membrane filtration, food processing, clarifiers, municipal sewage treatment, municipal water treatment, or potable water system.

In some embodiments, the water system is a surface that can be exposed to any water moisture.

In some embodiments, the fouling control composition or one or more cationic alkyl polyglucosides disclosed herein can mitigate microbial or biofilm growth in a water system as indicated by MBEC (Minimum Biofilm Eradication Concentration) assay, American Society for Testing and Materials (ASTM) MBEC-E2799-12 (2011) assay, or the similar essay described in the Examples section of this disclosure, when the water system has an alkyl polyglucoside, or mixture thereof concentration of from about 1 ppm to about 1,000 ppm, from about 1 to about 900 ppm, from about 1 ppm to about 800 ppm, from about 1 ppm to about 700 ppm, from about 1 ppm to about 600 ppm, from about 1 ppm to about 500 ppm, from about 1 ppm to about 400 ppm, from about 1 ppm to about 300 ppm, from about 1 ppm to about 250 ppm, from about 1 ppm to about 200 ppm, from about 1 ppm to about 150 ppm, from about 1 ppm to about 100 ppm, from about 1 ppm to about 50 ppm, from about 1 ppm to about 25 ppm, from about 1 ppm to about 10 ppm, from about 0.5 ppm to about 2 ppm, about 950 ppm, about 850 ppm, about 750 ppm, about 650 ppm, about 550 ppm, about 450 ppm, about 350, about 250 ppm, about 150 ppm, about 50 ppm, about 25 ppm, about 10 ppm, about 5 ppm, about 2 ppm, about 1 ppm, about 0.5 ppm or any value there between, after dosing the water system with the cationic alkyl polyglucoside, or mixture thereof, or the fouling control composition disclosed herein.

As used herein, the term "substantially free", "free" or "free of" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

EXAMPLES

Embodiments of the present disclosure are further defined in the following non-limiting Examples. These Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1

Effect of Some Cationic Polymeric Alkyl Poly Glucoside Compounds for Reducing Bacterial and Biofilm Growth Some exemplary cationic polymeric alkyl polyglucoside (APG) compounds were tested for their efficacy to reduce bacterial or biofilm growth in the example. The structures of the compounds tested in this example have a general structure as shown below. The specific $R^1$ and $R^2$ groups for each tested compound are listed in Table 2.

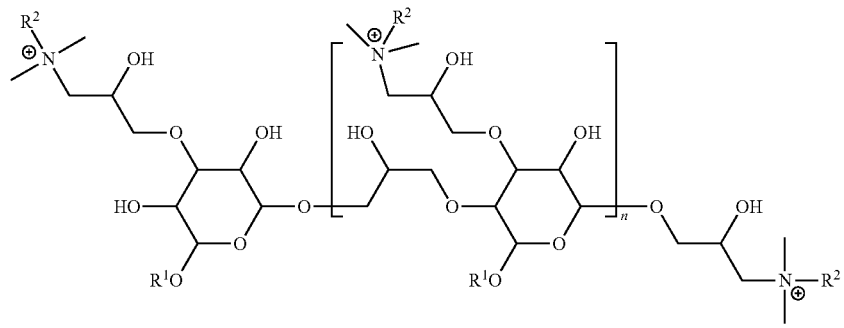

Two different compositions containing single quaternary compounds were also prepared for comparison purposes. Single Quat 1 sample comprises about 50% by weight bisoctyl dimethyl ammonium chloride (CAS #5538-94-3) and about 5-10% by weight glycerin; and Single Quat 2 sample comprises about 50% by weight didecyl-dimethyl ammonium chloride (CAS #7173-51-5) and about 10-30% by weight ethanol. Different concentrations of the exemplary one or more cationic alkyl polyglucosides and single quaternary compounds were tested ranging from about 0.8 ppm to about 1000 ppm.

The microbial and biofilm inhibition test protocols used in this example is like the MBEC (Minimum Biofilm Eradication Concentration) assay and American Society for Testing and Materials (ASTM) MBEC-E2799-12 (2011) assay, both of which are commonly used. This test protocol can be used laboratory and field applications.

The test protocol can be conducted in a 12-well or 96-well tissue culture plate format. The 12-well plate format is mainly for lab based and detailed screening/studies. The 96-well format is developed mainly for compound screening and field applications.

The test protocol starts with the preparation of the water samples to be tested by mixing the water from different water systems or artificial water with known bacterial populations with limited nutrient (16% of medium, 2% (w/w) casitone, 0.8% (w/w) yeast extracts, 4% (v/v) glycerol, 4 ppm $FeCl_3$) and the solution of the treatment chemical. This step usually generates a series of the treated water samples with different concentrations for the treatment chemical(s) (from about 0.8 ppm to 1,000 ppm).

Next, 200 μL of each treated water samples were transferred to a 96 well plate or 12 well plate. Usually, six replicates would be tested for each concentration of the treatment chemical(s) and controls with no treatment chemical and no bacterial were also placed in the plate(s). After the treated samples were properly plated, the plate(s) are placed on a slow rotary shaker in a humidity-controlled environment on at 32-35° C. for 40-48 hours of incubation.

After the incubation, the bacterial growth in each well of the plate was recorded either visually or by a microplate turbidity reader at 650 nm to determine the minimum bacterial growth inhibition concentration for a treatment chemical.

After this step, the bacterial cultures in the plate(s) were carefully poured out and 250 ul of dyes (350 ppm 2-(4-Iodophenyl)-3-(4-nitrophenyl)-5-phenyltetrazolium chloride (INT) or 2,000 ppm crystal violent (CV) for biofilm matrix stain) was added to each well for activity stain in biofilms on well walls. After 10-15 minutes, pour out the dye and gently wash the wells with deionized water until no colored water is running of the plate(s). After drying the plate(s), each well was inspected visually for staining and results are recorded.

Alternatively, use 300 uL ethanol to extract CV dyes and transfer 200 uL of ethanol to a new plate for microtiter plate recording at 590 nm. These results led to the determination of the minimum biofilm inhibition concentration of the treatment chemical or composition.

The bacteria used in this example for microbial and/or biofilm growth inhibition test protocols comprised a mixture of aerobic populations from more than 30 cooling systems in North America. The specific species were not specifically identified. Those species were grown on R2A agar.

The test results are shown in Table 3 and Table 4 and compared with the results obtained when two single quat compositions or no chemical was used. In Tables 3 and Table 4, "−" indicates no detectable growth at the end of test, "+" indicates detectable growth, "+/−" partial growth, "++" more growth.

TABLE 2

Cationic Polymeric Alkyl Poly Glucoside Compounds Tested
For Reducing Bacterial and Biofilm Growth

| ID | Structure or Name | R1 Group | R2 Group | MIC* (ppm) | MBEC** (ppm) |
|---|---|---|---|---|---|
| 1 | Poly Suga ® Quat L-1210P | C12 | C12 | 250 | 250 |
| 2 | Poly Suga ® Quat L-1010P | C12 | C10 | 125 | 250, 32 |
| 3 | Poly Suga ® Quat TM-8610P | C1 | C12-C18 | 1,000 | 1,000 |
| 4 | Poly Suga ® Quat S-1210P | C18 | C12 | 250 | 250 |
| 5 | H130 (single quat 1) | C10 | C10 | 50 | 25 |
| 6 | N90005 (single quat 2) | C8 | C8 | 500 | 1,000 |

MIC* minimum inhibition concentration of planktonic bacterial growth
MBEC** minimum biofilm elimination concentration

TABLE 3

Effect of Some Exemplary Polymeric Alkyl Poly Glucoside
Compounds for Reducing Bacterial Growth

| ID | \multicolumn{12}{c}{Test Concentration (ppm)} |
|---|---|---|---|---|---|---|---|---|---|---|---|---|

| ID | 0.8 | 1.5 | 3 | 6 | 12 | 25 | 50 | 63 | 125 | 250 | 500 | 1000 |
|---|---|---|---|---|---|---|---|---|---|---|---|---|
| 1 | + | + | + | + | + | ++ | ++ | + | + | − | − | − |
| 2 | + | + | + | + | + | + | + | +/− | − | − | − | − |
| 3 | + | + | + | + | + | + | + | + | + | + | +/− | +/− |
| 4 | + | + | + | + | + | + | + | + | + | − | − | − |
| 5 | + | + | ++ | ++ | + | +/− | − | − | − | − | − | − |
| 6 | + | + | + | + | + | + | ++ | + | + | +/− | − | − |
| Control (no chemical) | + | + | + | + | + | + | + | + | + | + | + | + |

TABLE 4

Effect of Some Exemplary Polymeric Alkyl Poly Glucoside
Compounds For Reducing Biofilm Growth

| ID | 0.8 | 1.5 | 3 | 6 | 12 | 25 | 50 | 63 | 125 | 250 | 500 | 1000 |
|---|---|---|---|---|---|---|---|---|---|---|---|---|
| 1 | + | + | + | + | +/− | +/− | +/− | +/− | +/− | − | − | − |
| 2 | + | + | + | + | + | − | − | +/− | +/− | − | − | − |
| 3 | + | + | + | + | ++ | ++ | + | + | + | +/− | +/− | − |
| 4 | + | + | + | + | +/− | +/− | +/− | +/− | +/− | − | − | − |
| 5 | + | + | +/− | +/− | +/− | − | − | +/− | +/− | − | − | − |
| 6 | + | + | + | + | + | ++ | ++ | ++ | +/− | +/− | +/− | − |
| Control (no chemical) | + | + | + | + | + | + | + | + | + | + | + | + |

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The disclosures being thus described, it will be obvious that the same may be varied in many ways. Such variations are not to be regarded as a departure from the spirit and scope of the disclosures and all such modifications are intended to be included within the scope of the following claims.

What is claimed is:

1. A method of controlling microbial fouling in a water system comprising:
providing a fouling control composition into a water system to generate a treated water system,
wherein the fouling control composition comprises a cationic alkyl polyglycoside, wherein the cationic alkyl polyglycoside is a cationic alkyl polyglucoside and comprises one or more glucose units and at least two cationic alkyl groups R—Y, wherein R is an alkyl group and Y is a cationic group; and
wherein the fouling control composition reduces bacterial growth or biofilm growth in the water system.

2. The method according to claim 1, wherein the cationic alkyl polyglucoside is one of

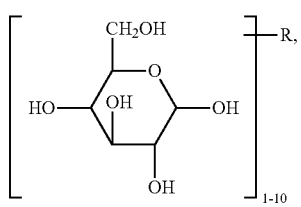

wherein the cationic alkyl polyglucoside comprises the at least two cationic alkyl groups R—Y.

3. The method according to claim 1, wherein the cationic alkyl polyglucoside comprises two or more glucose units and the glucose units are connected by glycosidic bond, a non-glycosidic bond, a linker, or a combination thereof.

4. The method according to claim 2, wherein R is a $C_1$-$C_{30}$ alkyl or $C_8$-$C_{24}$ alkyl, wherein Y is $NR^4R^5R^{6(+)}$, and $R^4$, $R^5$, and $R^6$ are independently $CH_3$, Y is $-NR^4R^5R^{6(+)}$, $R^4$ and $R^5$ are independently $CH_3$, and $R^6$ is a $C_2$-$C_{12}$ aromatic alkyl, Y is $-NR^4R^5R^{6(+)}$, $R^4$ and $R^5$ are independently $CH_3$, and $R^6$ is $-CH_2-C_6H_6$, or Y is $-NR^4R^5R^{6(+)}$ and the counter ion for the cationic group Y is chloride, bromide, fluoride, iodide, acetate, aluminate, cyanate, cyanide, dihydrogen phosphate, dihydrogen phosphite, formate, hydrogen carbonate, hydrogen oxalate, hydrogen sulfate, hydroxide, nitrate, nitrite, thiocyanate, or a combination thereof.

5. The method according to claim 1, wherein the cationic alkyl polyglucoside comprises three or more cationic alkyl groups R—Y.

6. The method according to claim 1, wherein the cationic alkyl polyglucoside further comprises one or more nonionic alkyl groups $R^3$, wherein $R^3$ is: an unsubstituted, linear, and saturated $C_1$-$C_{20}$ alkylene group; an unsubstituted, linear, and unsaturated $C_1$-$C_{20}$ alkylene group; a linear $C_8$-$C_{18}$ alkyl, alkenyl, or alkynyl group; or a branched $C_8$-$C_{20}$ alkyl, alkenyl, or alkynyl group.

7. The method according to claim 1, wherein the cationic alkyl polyglucoside is a single compound, or wherein the cationic alkyl polyglucoside is a mixture of two or more different alkyl polyglucosides, wherein the two or more different alkyl polyglucosides differ from each other by molecular weight, structure, net charge, or combination thereof.

8. The method according to claim 1, wherein the cationic alkyl polyglucoside has an average molecular weight of from about 200 to about 5,500 Da.

9. The method according to claim 1, wherein the cationic alkyl polyglucoside is

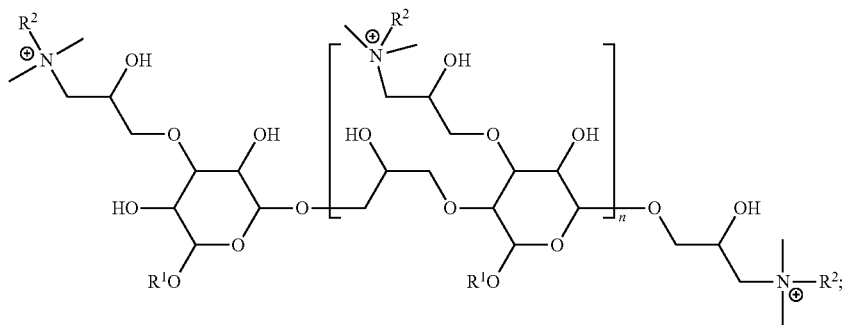

wherein n is 0-10, $R^1$ is a $C_1$-$C_{30}$ alkyl, and $R^1$ is a $C_1$-$C_{30}$ alkyl.

10. The method according to claim 1, wherein the cationic alkyl polyglucoside is soluble or dispersible in water or the fouling control composition.

11. The method according to claim 1, wherein the fouling control composition further comprises one or more fouling control composition agents, and wherein the fouling control composition comprises a carrier, wherein the carrier is water, an organic solvent, or a mixture thereof.

12. The method according to claim 11, wherein the organic solvent is an alcohol, a hydrocarbon, a ketone, an ether, an alkylene glycol, a glycol ether, an amide, a nitrile, a sulfoxide, an ester, or any combination thereof, or wherein the organic solvent is an alcohol, an alkylene glycol, an alkyleneglycol alkyl ether, or a combination thereof.

13. The method according to claim 12, wherein the organic solvent is methanol, ethanol, propanol, isopropanol, butanol, isobutanol, monoethyleneglycol, ethyleneglycol monobutyl ether, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, a mixture thereof with water, or any combination thereof.

14. The method according to claim 1, wherein the fouling control composition further comprises one or more of corrosion inhibitors, and wherein the corrosion inhibitor is an imidazoline compound, a pyridinium compound, or a combination thereof.

15. The method according to claim 1, wherein the fouling control composition further comprises an additional fouling control agent, wherein the additional fouling control agent a single quaternary compound, and optionally wherein the fouling control composition further comprises a biocide, wherein the biocide is chlorine, hypochlorite, $ClO_2$, bromine, ozone, hydrogen peroxide, peracetic acid, peroxycarboxylic acid, peroxycarboxylic acid composition, peroxysulphate, glutaraldehyde, dibromonitrilopropionamide, isothiazolone, terbutylazine, polymeric biguanide, methylene bisthiocyanate, tetrakis hydroxymethyl phosphonium sulphate, and any combination thereof.

16. The method according to claim 1, wherein the fouling control composition further comprises a preservative and/or an acid and wherein the fouling control composition comprises from about 1 wt-% to about 20 wt-% of the acid, and wherein the acid is hydrochloric acid, hydrofluoric acid, citric acid, formic acid, acetic acid, or mixture thereof.

17. The method according to claim 1, wherein the fouling control composition further comprises a hydrogen sulfide scavenger, and wherein the hydrogen sulfide scavenger is an oxidant, inorganic peroxide, sodium peroxide, chlorine dioxide; a $C_1$-$C_{10}$ aldehyde, formaldehyde, glyoxal, glutaraldehyde, acrolein, or methacrolein, a triazine, monoethanolamine triazine, monomethylamine triazine, or a mixture thereof.

18. The method according to claim 1, wherein the fouling control composition further comprises a surfactant, wherein the surfactant is a nonionic, semi-nonionic, cationic, anionic, amphoteric, zwitterionic, Gemini, di-cationic, di-anionic surfactant, or mixtures thereof, or wherein the surfactant is an alkyl phenol, fatty acid, or mixture thereof.

19. The method according to claim 1, wherein the fouling control composition further comprises an asphaltene inhibitor, a paraffin inhibitor, a scale inhibitor, a gas hydrate inhibitor, a pH modifier, an emulsion breaker, reverse emulsion breaker, coagulant/flocculant agent, an emulsifier, a water clarifier, a dispersant, antioxidant, polymer degradation prevention agent, permeability modifier, foaming agent, antifoaming agent, emulsifying agent, scavenger agent for $CO_2$, and/or $O_2$, gelling agent, lubricant, friction reducing agent, salt, or mixture thereof.

20. The method according to claim 1, wherein the fouling control composition is a liquid, gel, or a mixture comprising liquid/gel and solid, and wherein the fouling control composition or a use solution thereof has a pH of from about 2 to about 11.

21. The method according to claim 1, wherein the fouling control composition comprises from about 20 wt-% to about 60 wt-% of the cationic alkyl polyglycoside or mixture thereof, and/or wherein the cationic alkyl polyglycoside or mixture thereof has a concentration of from about 1 ppm to about 1000 ppm in the treated water system.

22. The method according to claim 21, wherein the cationic alkyl polyglucoside or mixture thereof is provided to the water system independently, simultaneously, or sequentially with one or more of the fouling control composition agents, and wherein the water system comprises fresh water, recycled water, salt water, surface water, produced water, or mixture thereof, or wherein the water system is a cooling water system, boiler water system, petroleum wells, downhole formations, geothermal wells, mineral washing, flotation and benefaction, papermaking, gas scrubbers, air washers, continuous casting processes in the metallurgical industry, air conditioning and refrigeration, water reclamation, water purification, membrane filtration, food processing, clarifiers, municipal sewage treatment, municipal water treatment, or potable water system.

23. The method according to claim 1, wherein the water system is a surface exposed to water moisture.

* * * * *

UNITED STATES PATENT AND TRADEMARK OFFICE
CERTIFICATE OF CORRECTION

PATENT NO. : 11,155,481 B2
APPLICATION NO. : 16/775417
DATED : October 26, 2021
INVENTOR(S) : Ashish Dhawan, Kun Xiong and Carter M. Silvernail It is certified that error appears in the above-identified patent and that said Letters Patent is hereby corrected as shown below:

In the Claims

<u>In Claim 9, at Column 37, Line 17:</u>
DELETE: "wherein n is 0-10, $R^1$ is a $C_1$-$C_{30}$ alkyl, and $R^1$ is a $C_1$-$C_{30}$ alkyl."
INSERT: --wherein n is 0-10, $R^1$ is a $C_1$-$C_{30}$ alkyl, and $R^2$ is a $C_1$-$C_{30}$ alkyl.--

Signed and Sealed this
Seventeenth Day of May, 2022

Katherine Kelly Vidal
*Director of the United States Patent and Trademark Office*